US009883826B2

(12) United States Patent
Jamieson et al.

(10) Patent No.: US 9,883,826 B2
(45) Date of Patent: Feb. 6, 2018

(54) IN VIVO BIOSENSOR (71) Applicant: DIAGNOSTIC BIOCHIPS, INC., Glen Burnie, MD (US)

(72) Inventors: Brian Jamieson, Glen Burnie, MD (US); Mary Emma Gorham Bigelow, Glen Burnie, MD (US)

(73) Assignee: DIAGNOSTIC BIOCHIPS, INC., Glen Burnie, MD (US)

( * ) Notice: Subject to any disclaimer, the term of this patent is extended or adjusted under 35 U.S.C. 154(b) by 0 days.

(21) Appl. No.: 14/413,257

(22) PCT Filed: Jul. 15, 2013

(86) PCT No.: PCT/US2013/050576
§ 371 (c)(1),
(2) Date: Jan. 7, 2015

(87) PCT Pub. No.: WO2014/014849
PCT Pub. Date: Jan. 23, 2014

(65) Prior Publication Data
US 2015/0164397 A1    Jun. 18, 2015

Related U.S. Application Data (60) Provisional application No. 61/672,281, filed on Jul. 16, 2012.

(51) Int. Cl.
*A61B 5/1473* (2006.01)
*A61N 1/36* (2006.01)
(Continued)

(52) U.S. Cl.
CPC ...... *A61B 5/14735* (2013.01); *A61B 5/04001* (2013.01); *A61B 5/0476* (2013.01);
(Continued)

(58) Field of Classification Search
None
See application file for complete search history.

(56) References Cited

U.S. PATENT DOCUMENTS 7,125,660 B2 * 10/2006 Stanton ............... C12Q 1/6825
435/4
8,167,871 B2 *  5/2012 Hyde .................... A61M 1/362
604/891.1

(Continued)

OTHER PUBLICATIONS

Citartan, M., et al., "Assays for aptamer-based platforms," Biosensors and Bioelectronics 2012;34:1-11.
(Continued)

*Primary Examiner* — Brian T Gedeon
(74) *Attorney, Agent, or Firm* — Cermak Nakajima & McGowan LLP; Malcolm K. McGowan (57) ABSTRACT

Certain embodiments comprise an implantable probe for rapid measurement of multiple neurochemicals on the cellular scale in the brain. Rapid detection of multiple chemicals in vivo (animal or humans) may provide an improved understanding of acute changes in neurochemicals that occur over several seconds. The neurotransmitter chemical sensing platform may provide for continuous in vivo sensing in trials of psychoactive drugs in the laboratory animal market. The high spatial resolution of the probe may allow for chemical detection around small groups of neurons, which may help to isolate the endogenous activity of different neuron types due to disease states. Neurochemical detection may also be used to measure tissue response to exogenous stimuli, such as pharmacodynamics of drugs. The high temporal and spatial resolutions and multi-neurochemical sensing of the probe may allow for detailed studies on in vivo brain response to both endogenous and exogenous stimuli.

50 Claims, 8 Drawing Sheets (51) Int. Cl.
*A61B 5/00* (2006.01)
*A61B 5/145* (2006.01)
*A61B 5/0476* (2006.01)
*A61B 5/04* (2006.01)
*A61N 1/05* (2006.01)
*B82Y 15/00* (2011.01)

(52) U.S. Cl.
CPC ........ *A61B 5/14546* (2013.01); *A61B 5/4836* (2013.01); *A61B 5/4845* (2013.01); *A61B 5/4848* (2013.01); *A61B 5/6852* (2013.01); *A61B 5/6876* (2013.01); *A61N 1/0534* (2013.01); *A61N 1/36139* (2013.01); *A61B 2562/028* (2013.01); *A61B 2562/125* (2013.01); *A61N 1/0529* (2013.01); *B82Y 15/00* (2013.01)

(56) References Cited

U.S. PATENT DOCUMENTS

| | | | |
|---|---|---|---|
| 8,346,482 B2* | 1/2013 | Fernandez | A61B 5/0215 702/19 |
| 8,370,070 B2* | 2/2013 | Fernandez | A61B 5/0215 702/19 |
| 2005/0023155 A1* | 2/2005 | Sawyer | G01N 33/5438 205/792 |
| 2008/0156646 A1 | 7/2008 | Wu et al. | |
| 2010/0262375 A1 | 10/2010 | Shachar et al. | |
| 2011/0087315 A1 | 4/2011 | Richardson-Burns et al. | |
| 2011/0150765 A1* | 6/2011 | Boyden | A61K 9/0019 424/9.1 |
| 2011/0237012 A1* | 9/2011 | Jang | G01N 33/5438 438/49 |
| 2012/0171715 A1* | 7/2012 | Thalhammer | G01N 33/48728 435/29 |

OTHER PUBLICATIONS

Liu, Z., et al., "Highly sensitive, reusable electrochemical aptasensor for adenosine," Electrochimica Acta 2009;54:6207-6211.
Song, S., et al., "Aptamer-based biosensors," Trends in Analytical Chemistry 2008;27(2):108-117.
Supplementary European Search Report for European Patent App. No. 13820353.4 (dated Jun. 1, 2016).

* cited by examiner

FIG. 1

Neural probes; (a) PEDOT sites, impedance 20-100kΩ;
(b) gold sites, impedance 3-5MΩ; (c) iridium sites,

IN VIVO BIOSENSOR

This application claims priority to U.S. Provisional Patent Application No. 61/672,281, filed Jul. 16, 2012, hereby incorporated by reference herein.

BACKGROUND OF THE DISCLOSURE

Technical Field of the Invention

Implementations consistent with the principles of the invention generally relate to the fabrication and use of aptamer-functionalized coatings and in particular to fabrication and use of aptamer-functionalized coatings to modify existing biosensors (neural probes) and make them specifically responsive to neurotransmitters.

Background

The development of micro-electro-mechanical systems (MEMS) has revolutionized the ability to deploy cost effective and high performance sensors for the continuous monitoring of a wide variety of parameters for automotive, biomedical, defense and industrial monitoring applications.

For example, most automobiles on the market today have sensors that continuously monitor for rapid decelerations in order to trigger airbag deployment, differential tire traction to apply anti-lock braking, and engine pressure and oxygen levels to adjust fuel mix. Oil quality sensors and other wear indicators provide diagnostics for engine and power train maintenance.

Similar instrumentation of the human body is beginning to be developed. Neuromodulation implants have been approved for use in humans for detecting and overriding a variety of neurological disorders such as Parkinson's and epilepsy. Implantable pressure sensors for monitoring patients following heart attack have shown great promise, as have implantable sensors for the continuous monitoring of glucose for the management of diabetes.

The full promise of implantable (in vivo) sensors for biomedical monitoring depends on substantial improvements to current implantable sensor technology, specifically the development of robust sensors that can unambiguously and accurately detect a wide variety of chemicals ("analytes"), and do so in a way that remains viable and accurate in the body for many months, if not years.

Currently, the only practical method to monitor drug concentrations in living and behaving lab animals is to draw blood and analyze it with lab instrumentation, a process that is time-consuming and expensive. Worse yet, if it is necessary to know the chemical concentration in a target tissue, it is necessary to sacrifice the animal, prepare a tissue sample, and run it through an analytical instrument such as HPLC. Again, this is expensive in that a large cohort of animals must be studied and sequentially sacrificed in order to explore drug concentrations at multiple endpoints. The ability to continuously monitor a drug or chemical concentration in a target tissue thus represents an enormous potential cost savings for those conducting pre-clinical trials and scientific studies.

Moreover, current sensing techniques have limited temporal and/or spatial resolution. For example, Microdialysis measures concentrations over a 2-20 minute collection period (typically around 15 minutes), resulting in average neurochemical measurements that obscure concentration changes associated with particular behaviors. Even when collected over a short time period, the accuracy of microdialysis measurements is largely diminished by factors (flow rate, percent recovery of in vivo concentration, etc.) that must be accounted for when converting analyte to in vivo concentrations. Enzyme-based biosensors can detect neurochemicals such as ethanol, glutamate, and dopamine with a 1-20 second response time, but have poor spatial resolution (0.5-1.0 mm) and can only detect one analyte per electrode. Finally, carbon-fiber electrode FSCV is able to collect dopamine, adenosine, and ascorbate concentrations with ms time response, but cannot reliably detect multiple chemicals simultaneously (Heinen et al, 2004).

However, electrochemical detection by FSCV has certain limitations including: 1) difficulty separating signals from similar compounds, such as enantiomers, or dopamine and norepinephrine (which vary by one hydroxyl group), 2) detection lifespan of 30 s-90 min, and 3) inability to detect electrically inactive molecules, such as glutamate and acetylcholine.

There is a need for systems and methods that address the shortcomings in the art.

SUMMARY OF THE INVENTION

Various systems and methods relating to integrating optical sources in semi-conductor based medical devices are disclosed and claimed.

In certain embodiments, a biosensor is disclosed, comprising: a substrate comprising one or more recording sites; and at least one aptamer affixed to one or more of the recording sites, wherein the at least one aptamer is selected to selectively react with one or more biochemicals. The at least one aptamer may be selected to selectively react to one or more chemical compounds specific to a test subject. The at least one aptamer may comprise one or more RNA nucleotide units. The at least one aptamer may comprise one or more DNA nucleotide units. The at least one aptamer may be locked. The at least one aptamer may comprise a small double-stranded section at the distal end to protect it from nuclease degradation, being made of at least one of DNA or RNA. The at least one aptamer may comprise one or more nucleotides with a 2'-O-methyl modification to reduce degradation by nuclease activity. The at least one aptamer may comprise a SOMAmer. The at least one aptamer may comprise one or more RNA nucleotide units. The at least one aptamer may comprise one or more disulfide bridges, a 3' cap with an inverted 2-deoxy thymidine, a 3'-3'-thymidine linkage at 3' terminus, a 2'-F modification, or any other modification intended to extend the half-life of the aptamer in vivo or to improve aptamer sensitivity, specificity, or binding kinetics. The substrate may comprise one or more elongated shanks for penetrating biological tissue and the one or more recording sites are located proximate the distal end of one or more of the elongated shanks for monitoring biological activity. The one or more elongated shanks may be between about 100 μm long and about 1 cm long. The one or more elongated shanks may be less than about 80 μm wide. Each of the one or more recording sites may be less than about 20 μm thick. The substrate may comprise at least one of glass, plastic and silicon. The biosensor may have a temporal resolution for measuring the concentrations of the one or more chemical compounds of less than about 4 seconds. The biosensor may have a spatial resolution for measuring the concentrations of the one or more chemical compounds of less or equal to about 50 μm.

In certain embodiments, a biosensor is disclosed, comprising: a microfabricated electrode array comprising one or more recording sites; and at least one aptamer affixed to one or more of the recording sites, wherein the at least one aptamer may be selected to selectively react with one or more chemical compounds. The microfabricated electrode array may be fabricated using at least one of photolithography, metallization and etching. The at least one aptamer may be selected to selectively react to one or more chemical compounds specific to a test subject. The biosensor may have a temporal resolution for measuring the concentrations of the one or more chemical compounds of less than about 4 seconds. The biosensor may have a spatial resolution for measuring the concentrations of the one or more chemical compounds of less or equal to about 50 µm.

In certain embodiments, a method of sensing biochemical concentration is disclosed comprising: providing a substrate comprising one or more recording sites; selecting one or more aptamers that selectively react with one or more chemical compounds; affixing the one or more aptamers to one or more recording sites on the substrate to form a biosensor; placing the one or more recording sites in vivo; and measuring the concentrations of one or more of the chemical compounds. The step of placing the one or more recording sites in vivo may comprise placing the one or more recording sites in the brain of a test subject; and the one or more chemical compounds comprise one or more clinically relevant biochemicals. The one or more chemical compounds may comprise dopamine. The one or more chemical compounds may comprise a neurotransmitter. The method may further comprise providing electrical stimulation to the brain of the test subject responsive to the measured concentrations of the one or more chemical compounds. The step of measuring may comprise measuring the concentration of a neurotransmitter in real time in the brain of a behaving animal or person. The method may further comprise recording neuronal electrical impulses or stimulation of electrical activity in target neuronal populations in the behaving animal or person. The method may further comprise stimulating electrical activity in target neuronal populations in the behaving animal or person. The step of placing the one or more recording sites in vivo may comprise placing the one or more recording sites in the blood stream of a test subject. The step of placing the one or more recording sites in vivo may comprise placing the one or more recording sites in the blood stream of a test subject. The step of placing the one or more recording sites in vivo may comprise placing the one or more recording sites in a selected one of an IV and a catheter and the step of measuring may comprise measuring a selected one of the gradient of the concentration and the flow rate of the one or more chemical compounds. The one or more aptamers may be selected by a process of molecule-based natural selection. The one or more aptamers may be selected to selectively react to a chemical compound specific to a test subject. The chemical compound may comprise a molecule engineered specifically for therapy in the test subject. The chemical compound may comprise a drug. The one or more aptamers may be selected based on at least one of speed of response to the one or more chemicals, affinity for bonding with one or more of the chemical compounds, and robustness in vivo. Robustness in vivo may comprise the ability to remain viable and active in vivo over time. The one or more aptamers may be selected for speed of bonding and unbonding with one or more of the chemical compounds to enable measurement of changes in the concentration of one or more of the chemical compounds over time. The step of measuring the concentrations has a temporal resolution of less than about 4 seconds. The step of measuring the concentrations has a spatial resolution of less or equal to about 50 µm. The one or more aptamers may be selected for sensitivity to a chemical compound that may be known to the provider of a sample and may be unknown to the device manufacturer. The chemical compound may be a selected one of a biomolecule and a drug.

In certain embodiments, a method of sensing biochemical concentration is disclosed comprising: implanting the biosensor of claim 1 into a test subject such that one or more of the recording sites may be located proximate biological tissue of a test subject; and measuring the concentrations of one or more of the chemical compounds in the biological tissue. The at least one aptamer may be selected to selectively react to one or more chemical compounds specific to a test subject. The method may further comprise transmitting the measured concentrations to an analysis unit remote from the test subject. The test subject may be a selected one of an animal and a human. The step of measuring the concentrations has a temporal resolution of less than about 4 seconds. The step of measuring the concentrations has a spatial resolution of less or equal to about 50 µm.

In certain embodiments a device is disclosed, comprising: a semiconductor chip; one or more recording sites integral to the chip; and at least one aptamer affixed to one or more of the recording sites, wherein the at least one aptamer may be selected to selectively react with one or more chemical compounds. The at least one aptamer may be selected to selectively react to one or more chemical compounds specific to a test subject. The semiconductor chip may comprise a substrate comprising one or more elongated shanks for penetrating biological tissue, each elongated shank comprising a proximal end and a distal end; and the one or more recording sites may be located proximate the distal end of one or more of the elongated shanks for monitoring biological activity. The one or more elongated shanks may be less than about 40 µm long. The one or more elongated shanks may be less than about 15 µm wide. Each of the one or more recording sites may be less than about 9 µm wide. The device may have a temporal resolution for measuring the concentrations of the one or more chemical compounds of less than about 4 seconds. The device may have a spatial resolution for measuring the concentrations of the one or more chemical compounds of less or equal to about 50 µm.

Other aspects and advantages of the present invention may be seen upon review of the figures, the detailed description, and the claims that follow.

BRIEF DESCRIPTION OF THE DRAWINGS

Some embodiments of the invention are described with reference to the following figures.

DETAILED DESCRIPTION

Certain embodiments comprise an implantable probe for rapid measurement of multiple neurochemicals on the cellular scale in the brain. The ability to follow changes in the brain is extremely important to understanding brain function for therapeutic opportunities. The ability of certain embodiments to rapidly detect multiple chemicals in vivo (animal or humans) may provide an improved understanding of acute changes in neurochemicals that occur over several seconds. Such data may reveal unstudied mechanisms behind disease states like seizures, or behaviors like drinking alcohol, that were previously obscured by the low temporal resolution of current methods. In certain embodiments, the neurotransmitter chemical sensing platform may provide for continuous in vivo sensing in trials of psychoactive drugs in the laboratory animal market.

In certain embodiments, the high spatial resolution of the probe allows for chemical detection around small groups of neurons, which may help to isolate the endogenous activity of different neuron types due to disease states. For example, studying dopamine-producing neurons and their role in Parkinson's disease has been used to develop a brain transplant therapy. Neurochemical detection may also be used to measure tissue response to exogenous stimuli, such as pharmacodynamics of drugs. In certain embodiments, the high temporal and spatial resolutions and multi-neurochemical sensing of the probe may allow for detailed studies on in vivo brain response to both endogenous and exogenous stimuli.

None of the currently available methods for neurochemical quantification (microdialysis, enzyme-based biosensors, or carbon-fiber microelectrode FSCV) is able to detect chemicals with both the temporal and spatial resolution of the probe of certain embodiments of the present invention. In certain embodiments, an implantable probe for the co-located electrical stimulation of neurons and subsequent measurement concentrations of multiple neurotransmitters may greatly improve understanding of the therapeutic mechanism of deep brain stimulation (DBS) on movement disorders. Integrating electrical stimulation and neurotransmitter detection has been attempted previously with fast scan cyclic voltammetry (FSCV) and enzyme-based sensors, but in certain embodiments the probe represents improved specificity and a broader range of detectable neurotransmitters over FSCV and improved spatial resolution and a multiple chemical detection advantage over enzyme-based sensing. In certain embodiments, a biosensor may collect multiple neurotransmitter concentrations every about 4 s on functionalized probe sites that are approximately 9 $\mu m^2$ and have an approximately 50 µm separation between stimulation sites and detection sites.

In certain embodiments, a biosensor may be used to specifically detect nearly any small molecule, based on the ability to generate an aptamer to any target. In certain embodiments, aptamers may be used to differentiate between L- and D-enantiomers. In certain embodiments, a biosensor may survive in vivo for 24 hours or more, allowing for more extended experimentation.

An aptamer may be made of RNA nucleotide units. An aptamer may be made of DNA nucleotide units. An aptamer may be "locked", or, includes a small double-stranded section at the distal end to protect it from nuclease degradation, being made of DNA or RNA. An aptamer may include nucleotides with a 2'-O-methyl modification to reduce degradation by nuclease activity. An aptamer may be a SOMAmer. An aptamer may include disulfide bridges, a 3' cap with an inverted 2-deoxy thymidine, a 3'-3'-thymidine linkage at 3' terminus, a 2'-F modification, or any other modification intended to extend the half-life of the aptamer in vivo or to improve aptamer sensitivity, specificity, or binding kinetics. Potential embodiments include but are not limited to a probe with aptamer-coated chemical recording sites and electrical recording sites; a probe with aptamer-coated chemical recording sites and electrical recording sites and electrical stimulation sites; a probe with additional technology to phase the exposure of aptamers to sample/tissue (for example, using the MICROchips technology to reveal new wells of aptamers in sequence) for the purpose of extending the useful in vivo life of the probe; a probe that combines aptamer-sensing technology with enzyme-based sensing or FSCV for improve temporal resolution (in the case of FSCV).

In certain embodiments, a biosensor may provide clearer indications for which brain structure to target (subthalamic nucleus or internal globus pallidus), and possibly indicate sub-structure areas that are best targeted for DBS. In certain embodiments, improved understanding of potential neurotransmitter signals from target brain regions and a technology that can rapidly measure neurotransmitters in vivo may be used for surgical guidance of implanted DBS electrodes or closed-loop control of DBS.

In certain embodiments, almost any neurotransmitter, including but not limited to dopamine and glutamate may be used as target molecules. The role of dopamine in DBS is controversial due to conflicting data collected using microdialysis, PET, and voltammetric microsensors. While voltammetry has detected a robust signal of dopamine release that is dependent on DBS parameters, microdialysis and PET imaging have not shown any increase in striatal dopamine levels. This discrepancy might be a result of the resolution of the microdialysis and PET techniques, which are not as good as the resolution of voltammetry. Additionally, clinical evidence shows that patients whose symptoms lessen in response to levodopa drug therapy (levodopa is metabolized into dopamine in the brain) experience better results from DBS, indicating some correlation between brain dopamine levels and DBS. In certain embodiments, the proposed probe may provide a high resolution technique (LOD=0.1 uM-10 uM) to provide more data for this debate on dopamine.

In certain embodiments, glutamate may be a suitable target molecule because it cannot be detected by FSCV, as it is not electrochemically active. Glutamate may be detected by coupling an enzyme with FSCV, but certain embodiments of a biosensor may have better spatial resolution than an enzyme-based sensor because the aptamer detection molecule is significantly smaller (10×) than enzymes. Glutamate may be relevant to a disease model because increased subthalamic nucleus (STN) output of glutamate (excitatory) may contribute to the degeneration of dopaminergic neurons, which causes Parkinson's disease. In certain embodiments, a biosensor probes may target one or more other important neurotransmitters, including but not limited to GABA, adenosine, and serotonin. Additionally, in certain embodiments, aptamers may be developed to enable a biosensor to detect concentrations of new therapeutic drugs (or levodopa). In certain embodiments, neurotransmitter responses may be monitored to determine drug efficacy. Indeed, in certain embodiments, a biosensor may be applicable to many neuroscience research applications beyond those directly related to DBS.

Certain embodiments combine high temporal and spatial resolution neural probes with a molecular layer for the detection of neurotransmitters. Certain embodiments integrate neurotransmitter detection with a stimulating electrode. Certain embodiments of the neurotransmitter detection technology disclosed and claimed herein may be applied to clinical DBS systems for novel surgical implantation guidance or closed-loop control methods. No currently commercially available products provide a neural probe with both electrical stimulation and neurotransmitter detection capabilities. Additionally, no commercially available probes can detect multiple neurochemicals on the spatial scale of certain embodiments of the present invention. In certain embodiments, aptamers may be used to rapidly and inexpensively develop a probe that is highly specific for most any stable molecule of interest to the neuroscientist.

Certain embodiments may provide a long-lasting, implantable probe that can both electrically stimulate neurons and rapidly measure multiple neurotransmitter concentrations for studying the effects of deep brain stimulation (DBS) on neuronal activity. The mechanism through which DBS reduces movement disorders in Parkinson's disease and tremor patients is largely unknown due to the limitations of existing techniques for recording neurotransmitter levels in vivo. In certain embodiments, a biosensor may be able to measure multiple neurotransmitters at the point of stimulation, which may reveal unknown cellular activity associated with Parkinson's disease and DBS. For example, conflicting data exists about the production of dopamine in the subthalamic nucleus in response to DBS. Research in this area with the proposed probe may result in improved understanding of which patients could benefit from DBS, or the best brain structure to target for DBS. In certain embodiments, neurotransmitter detection may be integrated on clinical stimulating electrodes, which may have applications in surgical electrode placement and closed-loop control of deep brain stimulation. Feasibility of using neurotransmitter concentrations in these applications may be explored by using a Parkinson's disease animal model for in vivo testing.

None of the currently available methods for neurotransmitter quantification (carbon microelectrode FSCV, microdialysis, and enzyme-based sensors) may be able to detect multiple chemicals with both the temporal and spatial resolution of certain embodiments of the present invention for an extended period of time (greater than 30 minutes). Carbon microelectrode FSCV samples with ms time response, but is limited to detecting only electroactive neurotransmitters (which includes dopamine, but excludes glutamate, acetylcholine) and can only collect data for 90 s-30 min. Microdialysis measures concentrations over a ~20 minute collection period, resulting in average neurochemical measurements that obscure concentration changes that occur immediately in response to DBS. Enzyme-based biosensors can detect neurochemicals such as ethanol, glutamate, and dopamine with a 1-20 second response time, but have poor spatial resolution (0.5-1.0 mm) and can only detect one analyte per electrode.

In certain embodiments, a biosensor may provide 50 µm spatial resolution between detection sites located around a stimulating electrode site, and a time response of <4 seconds, allowing it to detect multiple neurotransmitters on the cellular level in response to DBS-like stimulation. In certain embodiments, the foregoing temporal and spatial resolutions may enable detection of multiple neurochemicals on the cellular level in response to brief behavioral events, such as lever pressing in decision-making experiments.

In addition to high spatial and temporal resolution, certain embodiments of a biosensor may represent other advantages over current microdialysis, enzyme-based sensors, and FSCV. In certain embodiments, DNA aptamers may be used to detect analytes of interest. Aptamers may bind an analyte with fast kinetics, so analyte molecules may not be consumed or adsorbed as they are in other sensors. In certain embodiments, a biosensor may be used to study the brain in hypoxic conditions because it does not depend on oxygen for a detection reaction, as enzymes do. Aptamers do not induce an immune response like enzyme- or antibody-based sensors, which may result in less inflammation around an aptamer-based biosensor probe. In certain embodiments, a biosensor may have rectangular 40 µm×15 µm or may have 5-10 millimeter or longer shanks that will damage neural tissue much less than a typical ~300 µm diameter tip on the state-of-the-art enzyme-based biosensors. In certain embodiments, the reduced immune response and tissue damage may allow a biosensor to sense a less disrupted neuronal environment.

Currently, deep brain stimulation in patients operates at a continuous, high frequency. Once the electrode has been implanted, the patient sees their neurologist several times in the first 6-12 months with the implant to adjust the parameters of the stimulation. During this adjustment time, patients can experience considerable discomfort and side effects such as difficulty with speech. Deep brain stimulation is currently used in 80,000 US patients to alleviate movement disorders associated with Parkinson's Disease, such as rigidness, tremor, bradykinesia, dyskinesia, and dystonia. Currently, the FDA has approved the use of DBS to treat epilepsy and Parkinson's disease, but future approvals may include obsessive compulsive disorder, and depression. In certain embodiments, chemical sensing in accordance with certain embodiments of the present invention may be added to a DBS electrode, which may provide the following advantages over conventional DBS techniques: 1) more patients could benefit from DBS if it was easier to implement and had few side effects as may result from closed-loop control using chemical sensing, 2) neurochemical detection could be used to guide probe placement, resulting in better patient outcomes, and 3) neurotransmitter detection through chemical sensing is needed to study the mechanisms behind DBS as not much is known about how DBS works.

In certain embodiments, a biosensor may be used to study the mechanism with which DBS alleviates movement disorder symptoms. In certain embodiments, the biosensor may be used in patients after validation to establish a baseline of what neurotransmitter levels represent a good signal for surgical electrode placement and closed-loop control. In certain embodiments, a biosensor may allow for neurochemical sensing at the site of DBS and may be able to measure and record neurochemical levels during stimulation. In certain embodiments, a biosensor may be used for 1) proper placement of DBS electrode during surgical implantation and 2) closed-loop DBS for reduced side effects and longer battery life.

In certain embodiments, aptamers represent an advantage over enzyme-based sensors because, due to their small size, many more sensing units can fit on a small site, improving the spatial resolution that can be achieved over that of enzyme-based sensors. In certain embodiments, aptamer-based sensors with small site size, particular for individual neurotransmitters may equate to ability to sense multiple chemicals around a single neuron, whereas enzyme-based sensors can only detect a single chemical.

No commercially available probes can measure multiple neurochemical concentrations at the site of DBS. In certain embodiments, the foregoing aptamer-based approach may allow for the detection of neurotransmitters that cannot be detected using FSCV. In certain embodiments, the specificity of the aptamers will result in higher accuracy detection of multiple chemicals, whereas FSCV has poor resolution when it comes to deciphering multiple chemicals.

In certain embodiments, a MEMS process may be used for fabricating implantable, multi-site neural probes for studying the rat brain. In certain embodiments, some probe site surfaces of a multi-site neural probe may be functionalized with molecules for the detection of specific neurochemicals while other probe sites may be used to deliver electrical stimulation. In certain embodiments, detection of multiple neurochemicals may be achieved by patterning different neurochemical-specific detection molecules onto probe sites adjacent to the stimulation sites.

In certain embodiments, functionalized probe fabrication may be improved by adjusting aptamer molecule modifications, immobilization technique, and electrical signal detection to achieve the best possible sensitivity and time response for a particular application. In certain embodiments, a potentiostat circuit may be used for detection and current pulse for stimulation. In certain embodiments two aptamer molecules may be developed: one that is specific, sensitive, and long-lasting for dopamine, and another for glutamate. In certain embodiments, a biosensor probe may be functionalized the probe to detect multiple analytes with the newly developed aptamers. In certain embodiments, probes may be implanted into 6-OHDA unilateral lesioned (PD model) rats for in vivo data collection.

In certain embodiments, physiologically relevant concentrations of dopamine and glutamate may be accurately detected by probes that are stable in vivo for 48 hours. In certain embodiments, a microprocessor-based system may be used for the delivery of stimulation in response to neurotransmitter data. In certain embodiments, more aptamers may be applied to a biosensor for the detection of more than 2 neurotransmitters.

In certain embodiments, a method is provided for monitoring the in vivo concentration of a wide variety of molecules during "chronic" (e.g. long term) implantation or introduction into the body. The purpose for such an implantation might be medical, as in the monitoring of a particular biochemical response such as the release of a hormone or cancer marker, or the inflammatory response to an implanted device such as a neurostimulator. Alternatively, the purpose might be scientific, as in the monitoring of chemical concentrations such as neurotransmitters in the brains or other organs of laboratory animals. Certain embodiments may provide one or more of the following advantages over the state-of-the-art: (1) a wider variety of analytes can be sensed as compared to competing approaches (e.g. immunosensors, enzyme sensors); (2) the aptamer selection process allows you to control binding kinetics (this is not possible when using an organism to generate antibodies); (3) other biosensing elements can also be used on a biosensor in accordance with certain embodiments; (4) aptamer-based sensors "build themselves" (e.g. they are produced in a process of molecule-based natural selection) which means that sensor characteristics such as in vivo longevity and binding kinetics can be designed into them by controlling selection criteria; (5) sensors for multiple analytes can be located in very close physical proximity to each other, and implemented in custom geometries, for example as shown in FIGS. 3-8; and (6) spatial and temporal resolution may be improved compared to competitive approaches, which may be used in certain embodiments In certain embodiments, a biosensor may comprise a silicon neural recording probe with micron-scale recording sites ("functionalized sites"). In certain embodiments, aptamer-based biosensing elements permanently fixed to the surface of the recording sites may be used, other one of ordinary skill in the art will recognize that other biosensing elements may be used without departing from the scope of the present invention. In certain embodiments, the sites may allow the measurement of the concentration of an analyte of interest in vivo. In certain embodiments, an aptamer is a short chain of nucleotide bases that can be made selective for binding with an analyte of interest due to its tendency to fold on itself (similar to a folded protein such as an antibody or enzyme), thus creating a spatial "lock and key" geometry with the analyte. In certain embodiments, one or more methods may be used for reading out the signal generated by the functionalized sites subsequent to analyte binding. In certain embodiments, "reading out" may mean producing an electrical signal or other directly-measurable signal from the more fundamental physical change related to the binding of a chemical species to the aptamer. In certain embodiments, sites may be read out optically, in which case the aptamer would intentionally be engineered with a fluorescent marker molecule integrated into it, such that the conformational change of the aptamer during binding induces a change in the fluorescent properties of the aptamer, which would then be measured by exciting it with an optical source and measuring the output with an optical detector. In certain embodiments, an electrochemical readout may be used to exploit the changes in surface properties such as the proximity of reduction/oxidation (or redox) centers to an electrode (resulting in a current change signal), or changes in capacitance that result from conformational changes in the aptamer, or other biosensing element, that occur during binding of an analyte. In certain embodiments, an electrochemical readout might utilize impedance spectroscopy or cyclic voltammetry, or other approaches that are known in the field of electrochemistry. Alternatively, a readout based on some other physical principle might be used.

Figure 1:
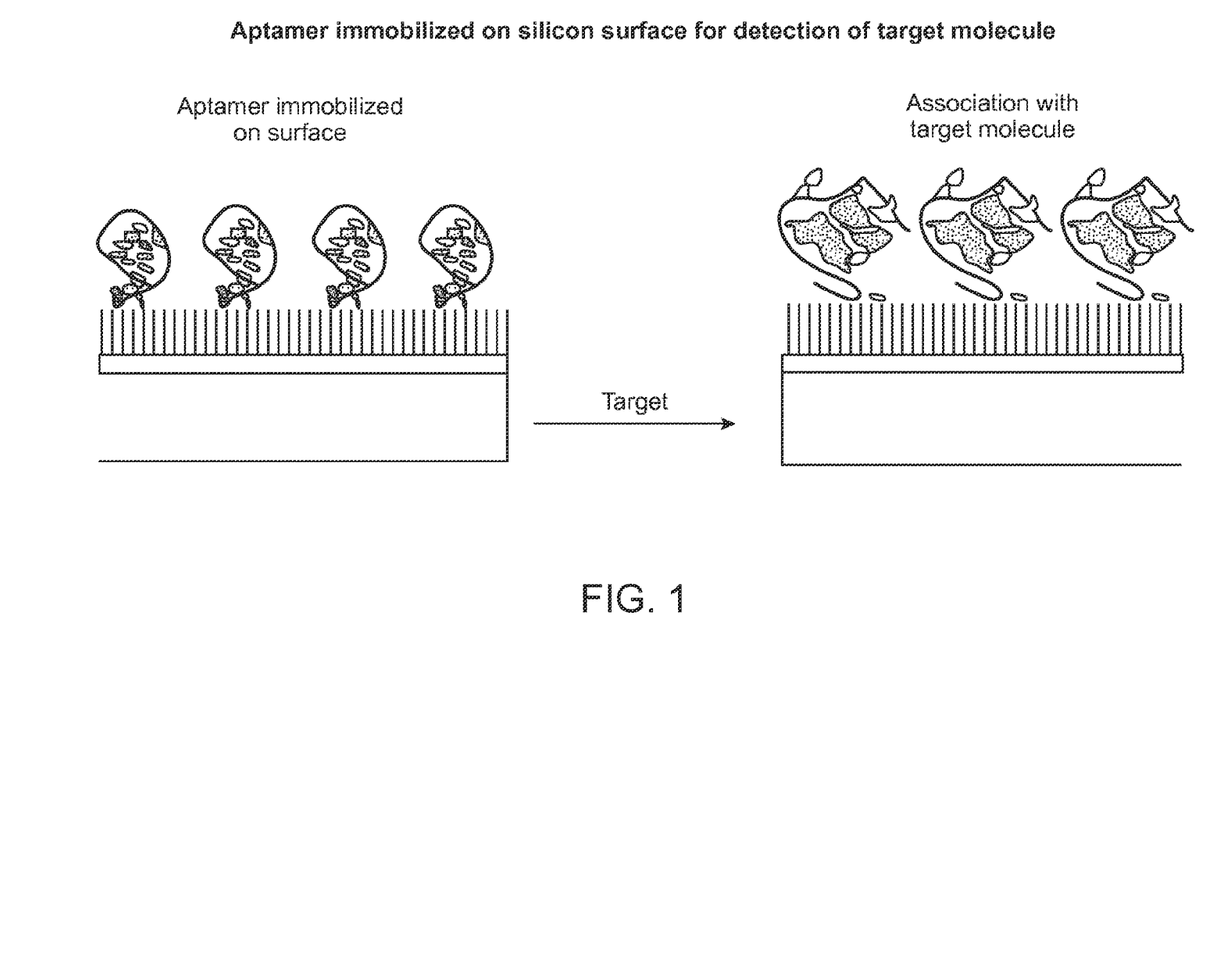
FIG. 1 depicts an aptamer immobilized on a silicon surface for detection of a target molecule in accordance with certain embodiments.
Figure 2:
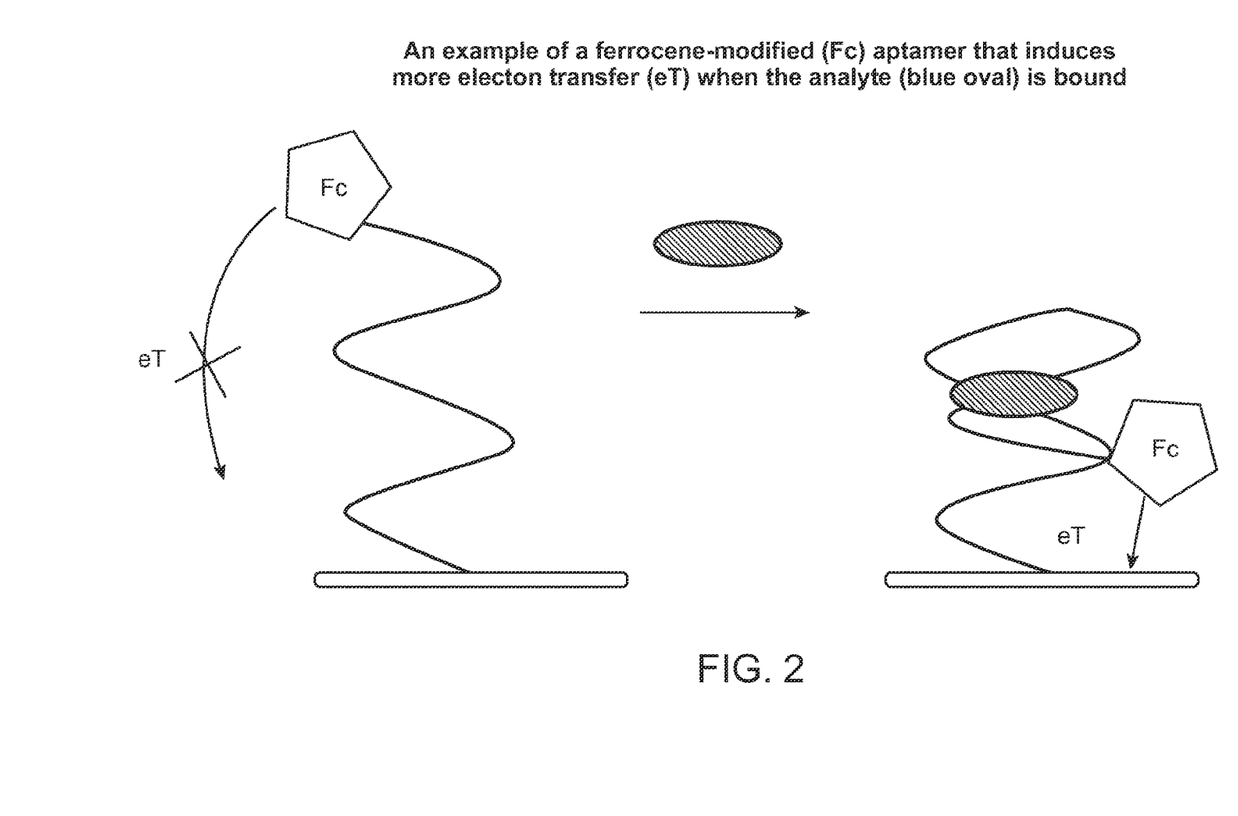
FIG. 2 depicts an example of a ferrocene-modified (Fc) aptamer that induces more electron transfer (eT) when the analyte (blue oval) is bound in accordance with certain embodiments.
Figure 3:
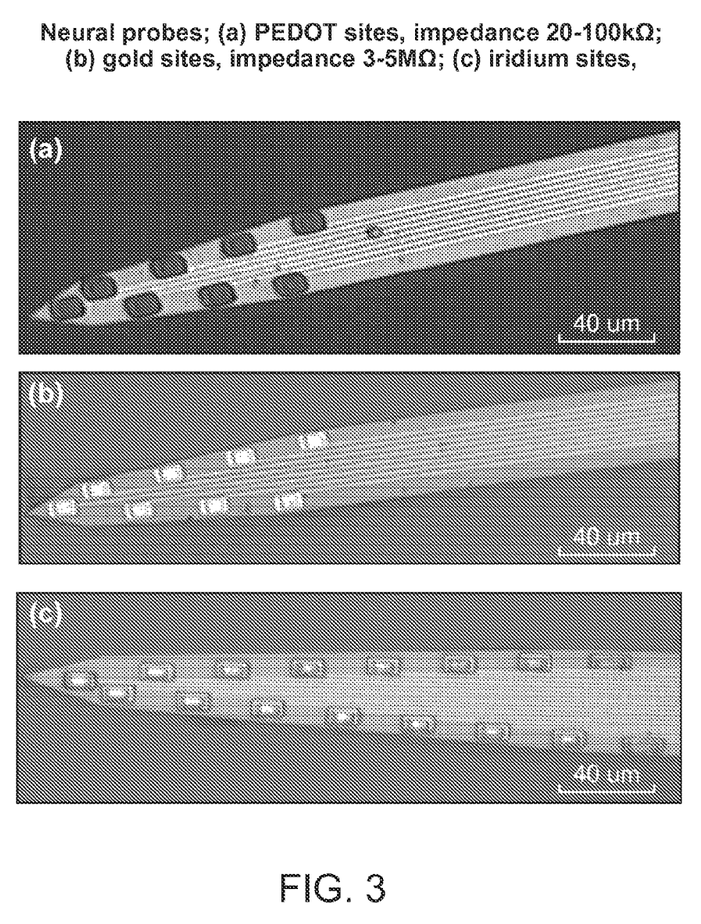
FIG. 3 depicts neural probes; (a) PEDOT sites, impedance 20-100 kΩ; (b) gold sites, impedance 3-5MΩ; (c) iridium sites in accordance with certain embodiments.
Figure 4:
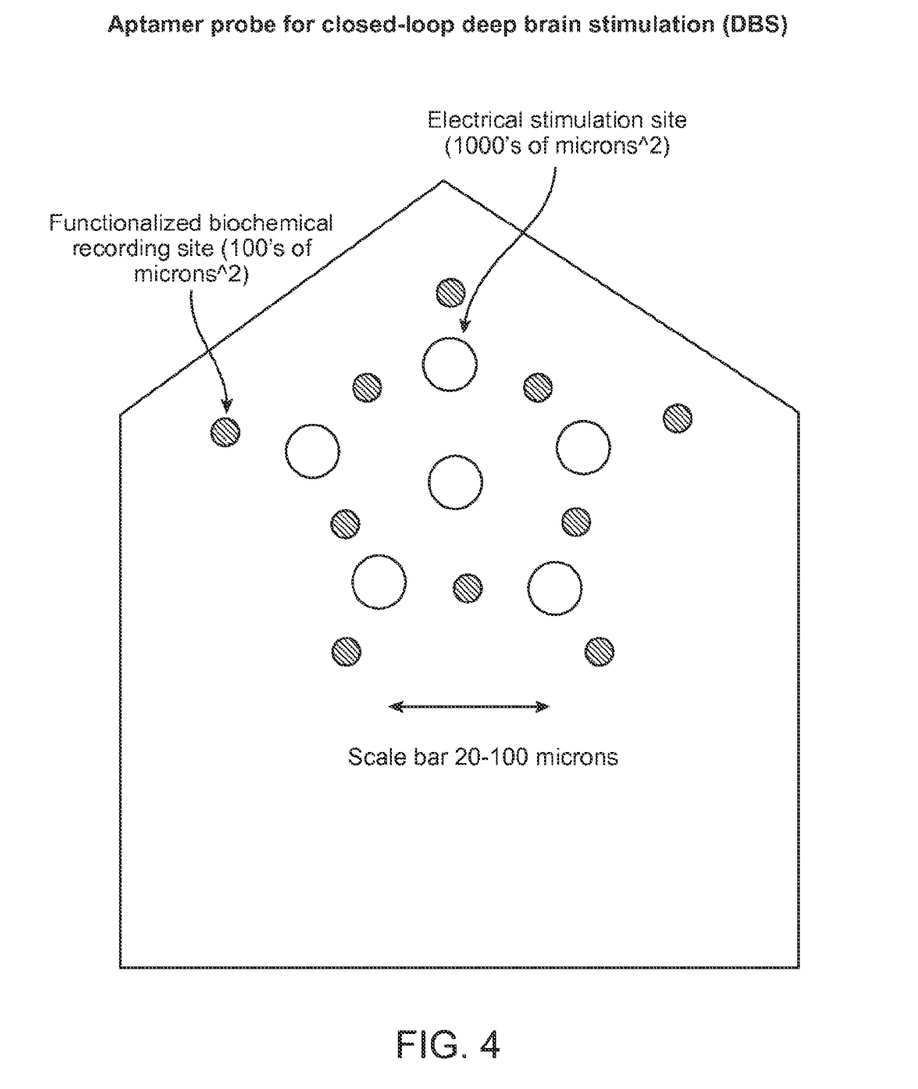
FIG. 4 depicts an aptamer probe for closed-loop deep brain stimulation (DBS) in accordance with certain embodiments.
Figure 5:
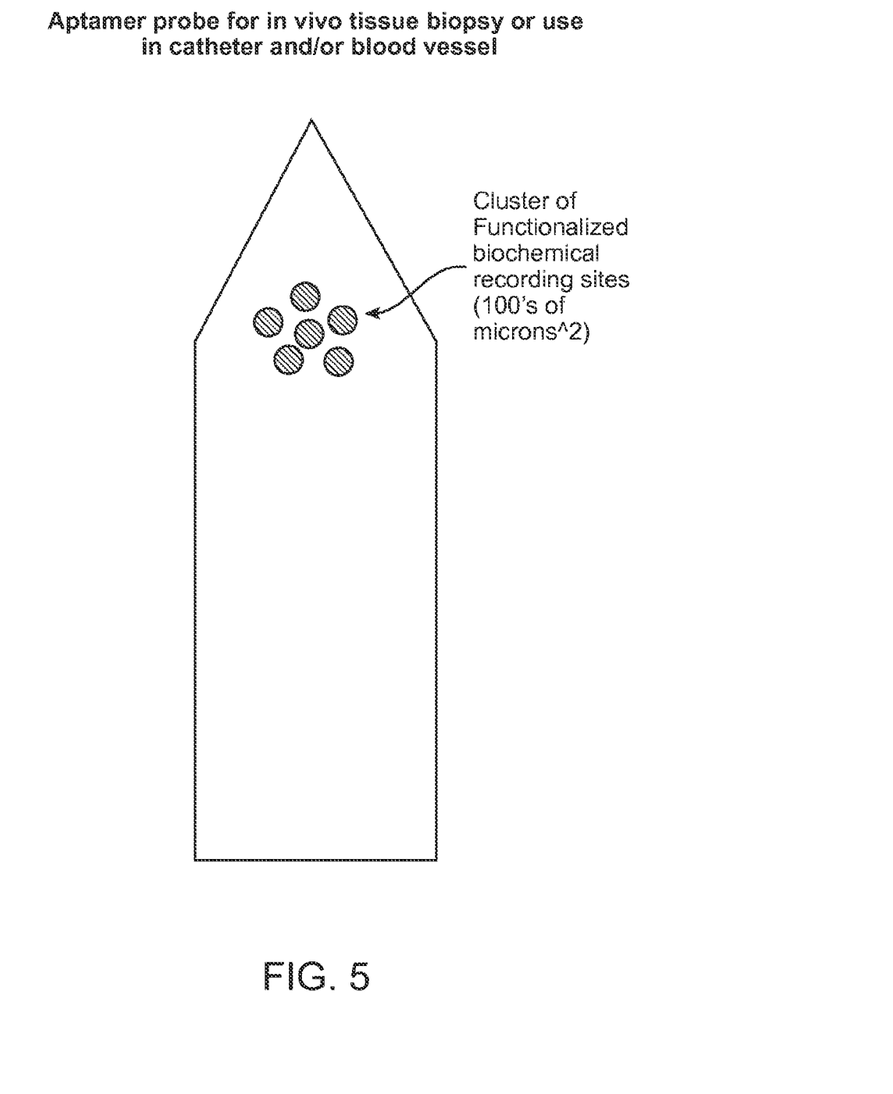
FIG. 5 depicts an aptamer probe for in vivo tissue biopsy or use in catheter and/or blood vessel in accordance with certain embodiments.
Figure 6:
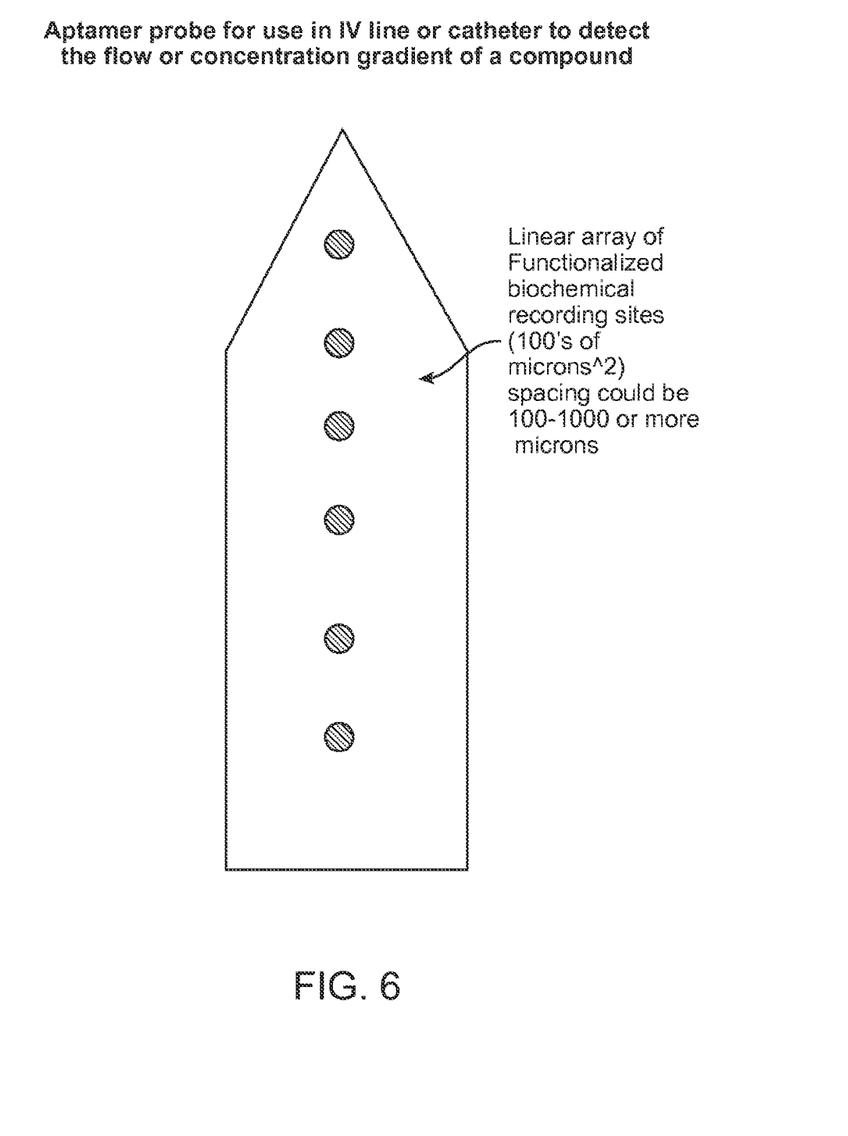
FIG. 6 depicts an aptamer probe for use in IV line or catheter to detect the flow or concentration gradient of a compound in accordance with certain embodiments.
Figure 7:
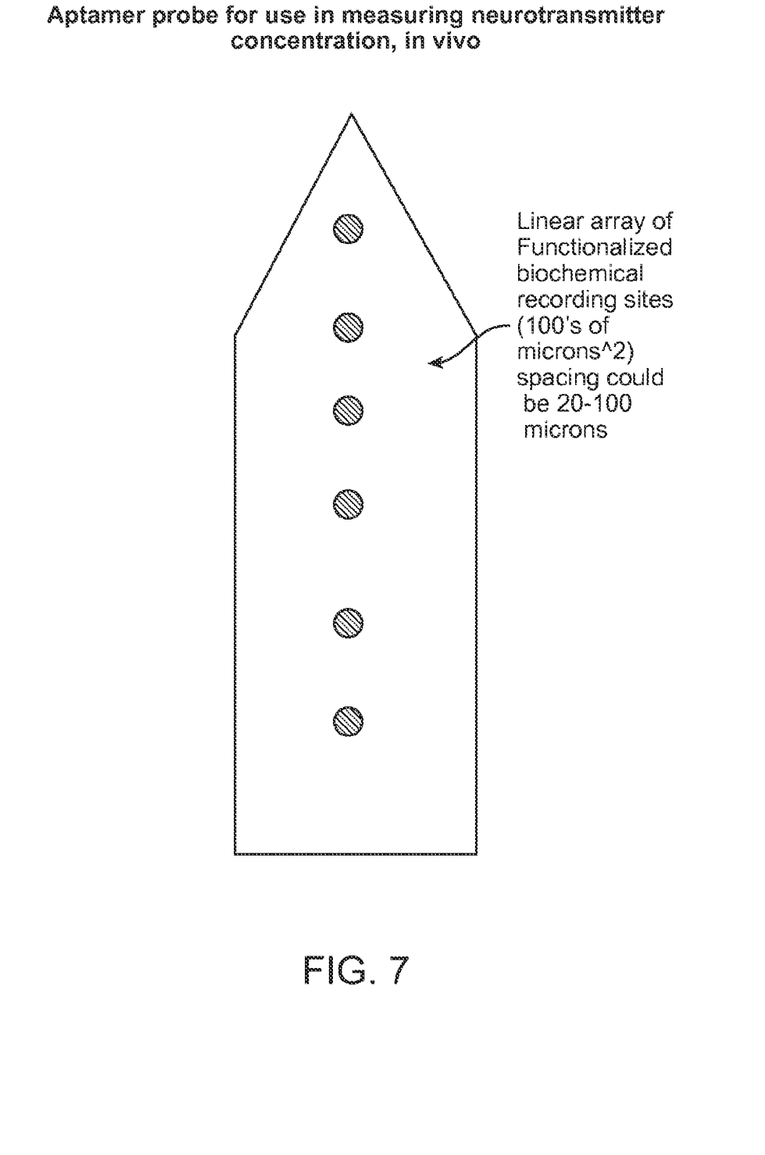
FIG. 7 depicts an aptamer probe for use in measuring neurotransmitter concentration, in vivo, in accordance with certain embodiments.
Figure 8:
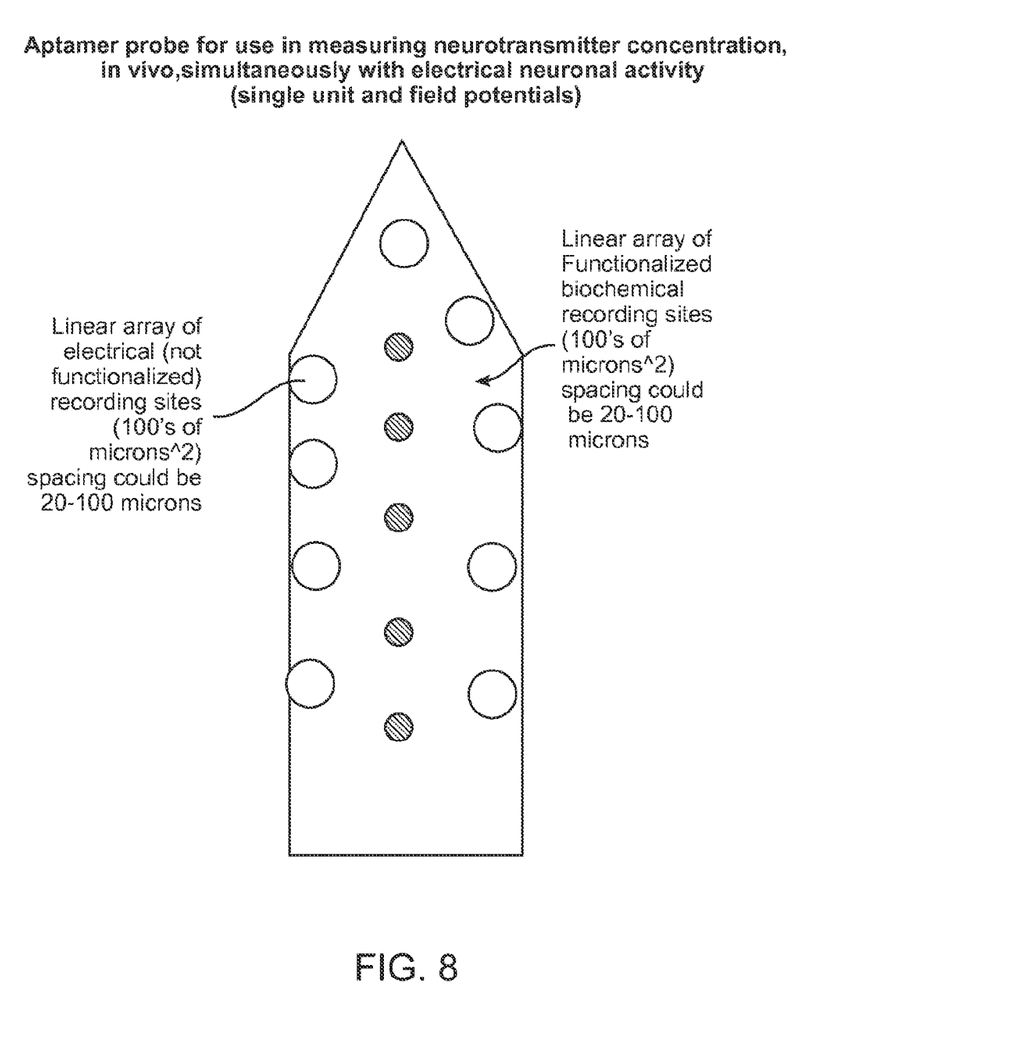
FIG. 8 depicts an aptamer probe for use in measuring neurotransmitter concentration, in vivo, simultaneously with electrical neuronal activity (single unit and field potentials) in accordance with certain embodiments.

In certain embodiments, a functionalized biosensing probe may comprise: a silicon neural probe substrate, patterned with micron scale metal recording sites as shown in FIG. 3; biosensing element-functionalized surfaces on recording sites as shown in FIGS. 1 and 2; and packaging as described below.

In certain embodiments, aptamers are nucleic acids (DNA or RNA) that may be engineered through many rounds of in vitro sequence selection to bind to various analytes, including small molecules, proteins, and cells. This process of DNA (or RNA) sequence selection is called SELEX (systematic evolution of ligands by exponential enrichment), which may be used to develop an aptamer with a specific binding affinity, specificity, or resistance to nuclease activity, among other factors. Aptamers may be analogous to antibodies in that affinity for target molecules is the result of structural interaction between the two molecules. FIG. 1 demonstrates a surface that has aptamers immobilized on a polymer thin film layer.

In certain embodiments as shown in FIG. 2, a silicon microfabrication process may be used to make probes with shank widths narrower than 40 nm and recording sites as small as 9 µm$^2$. This may enable fitting many recording channels in a micron-size area. In certain embodiments, the process may include first depositing dielectric material, followed by patterning of metal traces. A dielectric stack may then be deposited over the metal. After which, the contact vias may be etched to expose bondpads and recording sites of the probe. Functionalized metal or material may then patterned onto the device. Next, the probe outline may be etched from the front side, followed by a back side etch to release the neural probes. In certain embodiments, each of the steps in the probe fabrication process has been refined to improve device yield and probe quality.

FIG. 2 demonstrates how a ferrocene (Fc) molecule on the unanchored end of the aptamer can be moved closer to the electrode surface during analyte binding to induce a larger current.

In certain embodiments, one or more techniques may be used to alter the probe design and electrical qualities to meet requirements for a specific application. Photolithography may be used to pattern the neural electrodes, enabling fabrication of virtually any design. Depositing different metals or polymer thin films may be used to alter probe electrical qualities. For example, the biocompatible polymer PEDOT may be electroplate on probe sites as shown in FIG. 3a to reduce the impedance of gold probe sites as shown in FIG. 3b from about 3-5 MΩ to about 20-100 kΩ. In another process modification, probe sites may be coated with activated iridium oxide as shown in FIG. 3c to lower impedance and improve charge capacity.

The neural probe substrate need not necessarily consist of silicon, but may be some other semiconductor or polymer material, or other substrate entirely. In certain embodiments, the substrate is capable of being patterned by photolithographic and other micro-fabrication processes. In certain embodiments, silicon microfabrication may be used to process silicon neural probes with shank widths narrower than 40 µm and recording sites as small as 9 µm$^2$. Dielectric material may first be deposited followed by patterning of metal traces. A dielectric stack may then be deposited over the metal. Next the contact vias may be etched to expose bondpads and recording sites of the probe. This may be followed by etching the probe outline from the front side. Finally, etching may be performed from the back side to release the neural probes. The resulting biosensor need not be equivalent in shape to that shown in FIG. 3, but may have a variety of site arrangements, including but not limited to the exemplary arrangements shown in FIGS. 4-8. In certain embodiments, sites may be arranged in arrays or other arbitrary patterns designed in such a way as to make them useful for a particular target tissue or in vivo measurement. The overall shape of the biosensor probe need not be the same as shown in FIG. 3; in certain embodiments a more simplified shape or structure may be used such as a rectangular array of functionalized sites. The biosensor need not be used in vivo, but instead could be fabricated on a glass or plastic substrate, or other material, and used for in vitro diagnostics or similar applications such as point-of-care diagnostics or lab-on-a-chip, process monitoring or other industrial applications, biosensing for homeland security, and other applications known to those of ordinary skill in the art.

In certain embodiments, there are many methods that could be used for depositing aptamers, or other biosensing elements, specifically onto the probe recording sites, including but not limited to droplet spotting or any of a variety of contact or non-contact dispensing techniques, as well as spin coating, electroplating, and chemical vapor deposition. In spin coating or chemical vapor deposition, it may be useful to utilize a shadow mask or other similar masking feature during deposition, in order to pattern the aptamers, or other biosensing elements, specifically onto the sites. In certain embodiments, released neural probe sites may be patterned with electroplating a conductive polymer, such as polyanaline, onto the sites, and then chemically treating the polyanaline so that it bonds to the 5' or 3' end of the aptamer. In certain embodiments, a solution of the specific desired aptamer (concentrations 100 nM-100 µm) may be applied to an electroplate coat of i conducting polymer polyaniline (PANI). PANI is electroplated onto the probe sites by apply pulses (30 s-15 min), which may be 500 nA, while those sites are submerged in a analine monomer solution (around 0.1 M analine solution). In certain embodiments, applying current in PANI solution and subsequent aptamer immobilization may be repeated with other aptamers for all of the desired targets. In certain embodiments, PANI may be electroplated on all sites at once, and then different aptamers will be immobilized on separate sites in sequence. Aptamers may be immobilized on the conductive polymer surface (which may be PANI) by allowing the coated-probe to soak in a solution of aptamers, 1-ethyl-3-(3-dimethylaminopropyl) carbodiimide (EDC), and N-hydroxy-succinimide (NHS). To prevent nonspecific adsorption, either between deposition of different aptamers or after all aptamers are deposited, the aptamer-functionalized probe may be soaked in phosphate buffer saline (which may be 10 mM, pH 7.4) containing polyethyleneglycol-COOH (PEG-COOH) for 30 minutes to block the free sites on its surface. In order to confirm aptamer deposition, electrochemical impedance spectroscopy may be used to measure impedance on the electrode surface during target binding at various target concentrations. Further, in order to confirm correct specific aptamer deposition (in the case where more than one type of aptamer is applied), a fluorescently tagged complementary strand of DNA or RNA may be introduced to the probe in a solution, and then fluorescence may be observed with fluorescent microscopy. This method may be used to determine where aptamers are attached to the probe surface during any of the above functionalization methods. Certain embodiments may include alternative biosensing elements such as enzymes, antibodies, aptamers made of chains of amino acids or RNA (instead of DNA), SOMAmers, or polymer films with holes specifically shaped for analyte.

In certain embodiments, the functionalized biosensor may be packaged to connect the probe to an optical readout, a potentiostat or other suitable circuit, which may provide an electrical readout of the sensor. The output signal may be transmitted wirelessly. In certain embodiments that include aptamers as the biosensing element, aptamers would be selected for fast temporal response and for in vivo robustness. In certain embodiments, the subject invention may also be implemented on a modified chip platform suitable for implantation in a different part of the body, instead of the brain.

In certain embodiments, an in vivo biosensor may be inserted into the tissue of interest in a laboratory animal or human patient. The target tissue may be the brain or other organ, the blood stream, a subcutaneous area, a target tumor or any of a variety of other tissues or in vivo targets. In certain embodiments, the device may be fixed into place. In certain embodiments the device may be freely moving (such as in a capsule endoscope or other GI tract capsule.) There are many potential uses for such a device including in vivo biosensing for studying the concentration of naturally occurring biochemical or drugs, the penetration of candidate drugs into different tissues such as the brain or another organ, or the level of a clinically relevant chemical such as a cancer marker. In certain embodiments, a biosensor may be used either in vivo (e.g. in an implant) or in a diagnostic test or analytical (benchtop) instrument. The ability of this biosensor to detect small changes in multiple chemicals simultaneously, with very fast time response, and on a platform that does minimal damage to the tissue into which it is introduced leads to many potential applications. The monitoring of blood glucose level, stress hormones such as cortisol, or markers of cardiac distress are all potential applications for certain embodiments of the present invention, as is the surveillance of patients who have already experienced a medical problem (e.g. monitoring of CEA in survivors of colorectal cancer.)

One example application is the customized in vivo monitoring of the levels of an experimental drug in a laboratory animal or human patient. In studies involving the design and test of new drugs, the ability of a drug to penetrate a tissue of interest is difficult to test experimentally. Most commonly, the lab animal has to sacrificed, and the tissue has to be processed with analytical instrumentation to determine the concentration of the target drug. This may lead to several problems, including the fact that it is time and labor extensive, and the fact that it is impossible to monitor drug concentrations in a time series due to the fact that the animal is sacrificed. While there has been progress in recent years in developing biosensors capable of measuring in vivo drug concentrations, this technology is confounded by the fact that there is no 'universal detector' for chemistry, in the way that an appropriately calibrated LC/MS or CE instrument can detect a huge variety of drugs and chemicals without a priori knowledge. Typically, each biosensing molecule incorporated into a biosensor has to be painstakingly engineered for its affinity for the target molecule. In a paradigm in which large numbers of drugs are being screened, such an approach would be impossible to usefully exploit. Further, typical biosensors are not useful for detecting a wide range of non-protein based analytes. Certain embodiments of the present invention enable development of a customized biosensor for a new candidate drug (because the aptamer engineering process is fast and efficient) and then monitoring for the level of that drug in a target tissue. In certain embodiments, a similar approach may be used for personalized medicine; that is, the development of a custom sensor for the detection of a panel of compounds in one particular patient.

In certain embodiments, a long-lasting, implantable probe may be used for near real-time measurement of multiple neurochemicals in the brain. Certain embodiments may provide near real-time detection of concentrations of multiple neurochemicals with spatial resolution on the cellular level. In certain embodiments, a biosensor as disclosed above may allow neuroscience researchers to ask new questions about neural responses to stimuli. In certain embodiments, a neural probe may fulfill this need by detecting multiple (1, 2, or many) neurochemicals every 1 s with 50 μm spatial resolution. The high temporal resolution of the probes of certain embodiments of the present invention and sampling every <5 seconds may allow the detection of chemical concentrations during the brief behaviors involved in alcohol or drug consumption.

In certain embodiments, a biosensor may comprise feature size necessary for a 10-fold spatial resolution improvement over the available enzyme-based electrodes. In certain embodiments, the probe site surfaces may be chemically activated with molecules for the detection of specific neurochemicals. In certain embodiments, detection of multiple neurochemicals may be achieved by patterning different neurochemical-specific detection molecules onto adjacent probe sites.

In certain embodiments. functionalized probe fabrication may be improved or optimized by adjusting aptamer molecule modifications, immobilization techniques, and electrical signal detection to achieve the best possible sensitivity and time response, while in parallel, developing several aptamer molecules; ones that are specific, sensitive, and long-lasting for caffeine, cocaine, serotonin, dopamine, and GABA. In certain embodiments, a probe may be functionalized to detect multiple analytes with the newly develop aptamers. In certain embodiments, probes may be implanted into mice and rats for in vivo data collection.

In certain embodiments, the accurate detection of physiologically relevant concentrations of drugs and neurotransmitters may be provided by probes that are stable in vivo for an experimentally appropriate length of time (2 days-4 weeks). In certain embodiments, more aptamers may be applied to a probe for the detection of other neurotransmitters. In certain embodiments, the appropriate electrical testing protocol may be integrated into the data transmitter.

In certain embodiments, functionalized probe fabrication (aptamer molecule modifications, aptamer immobilization technique, and electrical signal detection) may be optimize to achieve a limit of detection of 0.2 μM with a signal-to-noise ratio of 3 and a response time of <5 seconds. In certain embodiments, aptamer molecules may be developed for the detection of ethanol and GABA that have limits of detection of 0.2 μM and 5.0 mM, respectively, (SNR>3) while maintaining a specificity of 0.01 over relevant interfering substances; develop aptamers to maximize lifespan in vitro. In certain embodiments, probes may be fabricated with ethanol and GABA aptamers immobilized on adjacent sites. In certain embodiments, the detection of ethanol minimize on a GABA site, and vice versa to achieve a sensor selectivity ratio >100:1. In certain embodiments, probes may be implanted into rats and mice to achieve a chronic implant lifespan in vivo. In certain embodiments, measurements may be compared with those of existing enzyme-based biosensors and microdialysis techniques.

While the invention has been described with reference to the specific embodiments thereof, it should be understood by those skilled in the art that various changes may be made and equivalents may be substituted without departing from the true spirit and scope of the invention as defined by the appended claims. In addition, many modifications may be made to adapt a particular situation, material, composition of matter, method, operation or operations, to the objective, spirit, and scope of the invention. All such modifications are intended to be within the scope of the claims appended hereto. In particular, while the methods disclosed herein have been described with reference to particular operations performed in a particular order, it will be understood that these operations may be combined, sub-divided, or re-ordered to form an equivalent method without departing from the teachings of the invention. Accordingly, unless specifically indicated herein, the order and grouping of the operations is not a limitation of the invention.

We claim:

1. A biosensor, comprising:
a substrate comprising one or more elongated shanks for penetrating biological tissue, and a microfabricated electrode array proximate the distal end of one or more of the elongated shanks, wherein the array comprises one or more recording sites; and
at least one aptamer affixed to one or more of the recording sites, wherein the at least one aptamer is selected to selectively react with one or more chemical compounds.

2. The biosensor of claim 1, wherein the at least one aptamer is selected to selectively react to one or more biochemical specific to a test subject.

3. The biosensor of claim 1, wherein the at least one aptamer comprises one or more RNA nucleotide units.

4. The biosensor of claim 1, wherein the at least one aptamer comprises one or more DNA nucleotide units.

5. The biosensor of claim 1, wherein the at least one aptamer is locked.

6. The biosensor of claim 1, wherein the at least one aptamer comprises a small double-stranded section at the distal end to protect it from nuclease degradation, being made of at least one of DNA or RNA.

7. The biosensor of claim 1, wherein the at least one aptamer comprises one or more nucleotides with a 2'-O-methyl modification to reduce degradation by nuclease activity.

8. The biosensor of claim 1, wherein the at least one aptamer comprises a SOMAmer.

9. The biosensor of claim 1, wherein the at least one aptamer comprises one or more RNA nucleotide units.

10. The biosensor of claim 1, wherein the at least one aptamer comprises one or more disulfide bridges, a 3' cap with an inverted 2-deoxy thymidine, a 3'-3'-thymidine linkage at 3' terminus, a 2'-F modification, or any other modification intended to extend the half-life of the aptamer in vivo or to improve aptamer sensitivity, specificity, or binding kinetics.

11. The biosensor of claim 1, wherein the one or more elongated shanks are between about 100 μm long and about 1 cm long.

12. The biosensor of claim 1, wherein the one or more elongated shanks are less than about 80 μm wide.

13. The biosensor of claim 1, wherein each of the one or more recording sites is less than about 20 μm thick.

14. The biosensor of claim 1, wherein the substrate comprises at least one of glass, plastic and silicon.

15. The biosensor of claim 1, wherein the biosensor has a temporal resolution for measuring the concentrations of the one or more chemical compounds of less than about 4 seconds.

16. The biosensor of claim 1, wherein the biosensor has a spatial resolution for measuring the concentrations of the one or more chemical compounds of less or equal to about 50 μm.

17. The biosensor of claim 1, wherein the microfabricated electrode array is fabricated using at least one of photolithography, metallization and etching.

18. The biosensor of claim 1, wherein the one or more elongated shanks are less than about 40 μm long.

19. The biosensor of claim 1, wherein the one or more elongated shanks are less than about 15 μm wide.

20. The biosensor of claim 1, wherein each of the one or more recording sites is less than about 9 μm wide.

21. The biosensor of claim 1, wherein the aptamer undergoes a conformational change upon binding with the selected compound.

22. The biosensor of claim 1, wherein the aptamer comprises a redox center.

23. A method of sensing biochemical concentration comprising: providing a biosensor according to claim 1; placing the one or more recording sites in vivo; and measuring the concentrations of one or more of the chemical compounds.

24. The method of claim 23, wherein the step of placing the one or more recording sites in vivo comprises placing the one or more recording sites in the brain of a test subject and wherein the one or more chemical compounds comprise one or more clinically relevant biochemicals.

25. The method of claim 23, wherein the one or more chemical compounds comprise dopamine.

26. The method of claim 23, wherein the one or more chemical compounds comprise a neurotransmitter.

27. The method of claim 23, further comprising providing electrical stimulation to the brain of the test subject responsive to the measured concentrations of the one or more chemical compounds.

28. The method of claim 23, wherein the step of measuring comprises measuring the concentration of a neurotransmitter in real time in the brain of a behaving animal or person.

29. The method of claim 23, further comprising recording neuronal electrical impulses or stimulation of electrical activity in target neuronal populations in the behaving animal or person.

30. The method of claim 23, further comprising stimulating electrical activity in target neuronal populations in the behaving animal or person.

31. The method of claim 23, wherein the step of placing the one or more recording sites in vivo comprises placing the one or more recording sites in the blood stream of a test subject.

32. The method of claim 23, wherein the step of placing the one or more recording sites in vivo comprises placing the one or more recording sites in the blood stream of a test subject.

33. The method of claim 23, wherein the step of placing the one or more recording sites in vivo comprises placing the one or more recording sites in a selected one of an IV and a catheter and the step of measuring comprises measuring a selected one of the gradient of the concentration and the flow rate of the one or more chemical compounds.

34. The method of claim 23, wherein the one or more aptamers are selected by a process of molecule-based natural selection.

35. The method of claim 23, wherein the one or more aptamers are selected to selectively react to a chemical compound specific to a test subject.

36. The method of claim 23, wherein the chemical compound comprises a molecule engineered specifically for therapy in the test subject.

37. The method of claim 23, wherein the chemical compound comprises a drug.

38. The method of claim 23, wherein the one or more aptamers are selected based on at least one of speed of response to the one or more chemicals, affinity for bonding with one or more of the chemical compounds, and robustness in vivo.

39. The method of claim 38, wherein robustness in vivo comprises the ability to remain viable and active in vivo over time.

40. The method of claim 23, wherein the one or more aptamers are selected for speed of bonding and unbonding with one or more of the chemical compounds to enable measurement of changes in the concentration of one or more of the chemical compounds over time.

41. The method of claim 23, wherein the step of measuring the concentrations has a temporal resolution of less than about 4 seconds.

42. The method of claim 23, wherein the step of measuring the concentrations has a spatial resolution of less or equal to about 50 μm.

43. The method of claim 23, wherein the one or more aptamers are selected for sensitivity to a chemical compound that is known to the provider of a sample and is unknown to the device manufacturer.

44. The method of claim 23, wherein the chemical compound is a selected one of a biomolecule and a drug.

45. A method of sensing biochemical concentration comprising: implanting the biosensor of claim 1 into a test subject such that one or more of the recording sites are located proximate biological tissue of a test subject; and measuring the concentrations of one or more of the chemical compounds in the biological tissue.

46. The method of claim 45, wherein the at least one aptamer is selected to selectively react to one or more chemical compounds specific to a test subject.

47. The method of claim 45, further comprising transmitting the measured concentrations to an analysis unit remote from the test subject.

48. The method of claim 45, wherein the test subject is a selected one of an animal and a human.

49. The method of claim 45, wherein the step of measuring the concentrations has a temporal resolution of less than about 4 seconds.

50. The method of claim 45, wherein the step of measuring the concentrations has a spatial resolution of less or equal to about 50 μm.

* * * * *